(12) United States Patent
Abbruzzese (10) Patent No.: US 10,431,109 B2
(45) Date of Patent: Oct. 1, 2019

(54) SYSTEMS AND METHODS FOR SOMATIZATION IDENTIFICATION AND TREATMENT

(71) Applicant: Cambia Health Solutions, Inc., Portland, OR (US)

(72) Inventor: Evgenia Abbruzzese, Portland, OR (US)

(73) Assignee: Cambia Health Solutions, Inc., Portland, OR (US)

( * ) Notice: Subject to any disclaimer, the term of this patent is extended or adjusted under 35 U.S.C. 154(b) by 302 days.

(21) Appl. No.: 15/173,440

(22) Filed: Jun. 3, 2016

(65) Prior Publication Data
US 2016/0358501 A1    Dec. 8, 2016

Related U.S. Application Data

(60) Provisional application No. 62/170,621, filed on Jun. 3, 2015.

(51) Int. Cl.
*G09B 5/02* (2006.01)
*G16H 40/67* (2018.01)
(Continued)

(52) U.S. Cl.
CPC .............. *G09B 5/02* (2013.01); *G16H 10/60* (2018.01); *G16H 20/70* (2018.01); *G16H 40/67* (2018.01); *G16H 50/20* (2018.01)

(58) Field of Classification Search
CPC .......... G06F 19/30; G09B 5/02; G16H 10/60; G16H 20/70; G16H 40/67
See application file for complete search history.

(56) References Cited

U.S. PATENT DOCUMENTS

| 5,435,324 A | 7/1995 | Brill |
| 5,486,999 A * | 1/1996 | Mebane ............... G06Q 50/22 705/2 |

(Continued)

OTHER PUBLICATIONS

Barsky, A. et al., "Distinctive Patterns of Medical Care Utilization in Patients Who Somatize," Medical Care, vol. 44, No. 9, Sep. 2006, 9 pages.

*Primary Examiner* — Xuan M Thai
*Assistant Examiner* — Malina D. Blaise
(74) *Attorney, Agent, or Firm* — McCoy Russell LLP (57) ABSTRACT

Systems and methods for somatization system are provided. Specifically, systems and methods are provided for identifying somatizing patients suffering from one or more physical symptoms that are in excess of demonstrable injury, illness, or disease. In one example, a method may comprise receiving medical claims data for a plurality of patients, identifying somatizing patients based on the received medical claims data, where the somatization patients include patients suffering from one or more physical symptoms that are being amplified as a result of somatization, presenting a symptom support plan to the identified somatization patients via a user interface based on a severity of their disorder, where the symptom support plan may include one or more of educational programs, episodic support, and mental health therapy. In some examples, the method may additionally include monitoring identified somatization patients' progress in the symptom support plan, and displaying the patient's progress to a health plan provider.

16 Claims, 9 Drawing Sheets

(51) Int. Cl.
*G16H 10/60* (2018.01)
*G16H 50/20* (2018.01)
*G16H 20/70* (2018.01)

(56) References Cited

U.S. PATENT DOCUMENTS

| | | | |
|---|---|---|---|
| 6,269,339 B1 | 7/2001 | Silver | |
| 6,391,922 B1* | 5/2002 | Fogel | A61K 31/00 |
| | | | 514/702 |
| 6,425,764 B1* | 7/2002 | Lamson | A61M 21/00 |
| | | | 434/236 |
| 7,097,617 B1* | 8/2006 | Smith | A61B 5/4824 |
| | | | 600/300 |
| 7,493,264 B1 | 2/2009 | Kelly et al. | |
| 7,593,952 B2* | 9/2009 | Soll | G06F 19/322 |
| 7,835,997 B2 | 11/2010 | Rajkhowa et al. | |
| 8,032,398 B1 | 10/2011 | Kelly et al. | |
| 8,095,380 B2 | 1/2012 | Wennberg | |
| 8,290,789 B2 | 10/2012 | Wennberg | |
| 8,484,085 B2 | 7/2013 | Wennberg | |
| 8,718,245 B2 | 5/2014 | Kahn | |
| 2001/0020229 A1 | 9/2001 | Lash | |
| 2002/0128868 A1* | 9/2002 | Lonski | G06F 19/328 |
| | | | 705/2 |
| 2002/0143582 A1 | 10/2002 | Neuman et al. | |
| 2003/0059750 A1 | 3/2003 | Bindler et al. | |
| 2003/0144886 A1* | 7/2003 | Taira | G06Q 10/10 |
| | | | 705/3 |
| 2006/0064319 A1 | 3/2006 | Loevner | |
| 2006/0116557 A1 | 6/2006 | Moore et al. | |
| 2006/0150989 A1* | 7/2006 | Migaly | A61B 5/165 |
| | | | 128/898 |
| 2007/0050215 A1 | 3/2007 | Kil et al. | |
| 2007/0072156 A1 | 3/2007 | Kaufman et al. | |
| 2007/0166690 A1 | 7/2007 | Johnson | |
| 2007/0219824 A1* | 9/2007 | Rawlings | G06F 19/328 |
| | | | 705/2 |
| 2008/0262982 A1 | 10/2008 | Rajkhowa et al. | |
| 2009/0240529 A1 | 9/2009 | Chess et al. | |
| 2010/0198755 A1* | 8/2010 | Soll | G06F 19/324 |
| | | | 706/11 |
| 2010/0274579 A1 | 10/2010 | Marten et al. | |
| 2011/0060688 A1* | 3/2011 | Fernandez Gutierrez | |
| | | | G06Q 30/02 |
| | | | 705/55 |
| 2011/0191120 A1 | 8/2011 | Laskoff et al. | |
| 2011/0301982 A1* | 12/2011 | Green, Jr. | G06Q 10/06 |
| | | | 705/3 |
| 2012/0185275 A1* | 7/2012 | Loghmani | G06F 19/328 |
| | | | 705/3 |
| 2012/0197660 A1* | 8/2012 | Prodanovich | G06Q 30/04 |
| | | | 705/2 |
| 2012/0209620 A1 | 8/2012 | Ebadollahi et al. | |
| 2013/0117040 A1 | 5/2013 | James et al. | |
| 2013/0185096 A1* | 7/2013 | Giusti | G06Q 50/24 |
| | | | 705/3 |
| 2014/0004492 A1 | 1/2014 | O'Reilly et al. | |
| 2014/0046693 A1 | 2/2014 | Wennberg | |
| 2014/0214442 A1 | 7/2014 | Duffy et al. | |
| 2014/0214443 A1 | 7/2014 | Duffy et al. | |
| 2014/0222454 A1 | 8/2014 | Duffy et al. | |
| 2014/0229547 A1 | 8/2014 | Justin | |
| 2014/0315170 A1 | 10/2014 | Ionescu et al. | |
| 2015/0019255 A1 | 1/2015 | Coetzer | |
| 2016/0005320 A1* | 1/2016 | deCharms | G09B 5/065 |
| | | | 434/236 |

* cited by examiner

SYSTEMS AND METHODS FOR SOMATIZATION IDENTIFICATION AND TREATMENT

CROSS REFERENCE TO RELATED APPLICATIONS

The present application claims priority to U.S. Provisional Patent Application No. 62/170,621, entitled "SYSTEMS AND METHODS FOR SOMATIZATION IDENTIFICATION AND TREATMENT," and filed on Jun. 3, 2015, the entire contents of which are hereby incorporated by reference for all purposes.

BACKGROUND/SUMMARY

In many modern health care systems there is an established protocol that patients follow for receiving medical treatment when suffering from one or more physical illnesses, injuries, diseases etc. A patient may experience symptoms, determine whether or not to seek medical assistance based on the severity of their symptoms, and then may visit a care provider to ascertain a diagnosis and treatment plan to cure and/or alleviate their symptoms. In some examples, the care provider may render a diagnosis and prescribe a treatment plan for the patient. In other examples, the care provider may decide to refer the patient to a medical expert specializing in a field of medicine related to the patient's illness, disease, injury, etc.

However, in some cases, patients may experience physical symptoms, for which there is no underlying physical cause or medical explanation. This condition is commonly referred to as somatic symptom disorder. Said another way, patients may report subjective experiences of the symptoms associated with one or more diseases, but doctors cannot find an objective verification of the symptoms without a structural problem that would explain subjective patient experiences. These symptoms have been called "Medically Unexplained Symptoms," or MUS. In these instances, the symptoms may be caused by anxiety, stress, or other mental health disorders, or could be caused by a functional condition for which no effective diagnostic tool exists. However, patients with MUS symptoms unwittingly engage in symptom-amplifying behaviors and thoughts. These types of patients that experience physical symptoms disproportionate to the underlying disease or condition as a result of symptoms amplification, may be referred to in the description herein as somatization patients.

However, many health care providers do not have sufficient information to assess whether the patient's tendency to somitize is contributing to the symptom manifestation, nor do they have access to an evidence-based intervention to help the psychological needs underlying this tendency. It is estimated that approximately 10% of health care associated costs are spent in attempts to diagnose persistent symptoms reported by this population of patients. Thus, the healthcare system is expanding significant resources to diagnose symptoms which are not medically-based. As such, money in the health care system may be wasted by incorrectly diagnosing and treating patients with mental health disorders. More specifically, both patients, health plans, and providers may be spending money on repeat diagnostics and improper treatments. The improper identification, diagnosis, and treatment of somatization patients may be in part due to one or more of the difficulty in distinguishing and identifying somatization patients from other patients with physical conditions at first presentation, convincing somatization patients to engage in mental health therapies, and delivering the proper mental health therapies to the somatization patients.

Somatization patients may be difficult to find and identity for many reasons. Physicians often struggle to identify somatization patients because patients may frequently switch health care providers. Further, somatization patients are often sensitive about their conditions, and in many cases are afraid or unwilling to identify themselves. Further, most somatization patients are unaware of their mental disorder and do not link physical symptoms with health anxiety. Family member of somatization patients, which could be helpful in identifying somatization patients, may have difficulty linking symptoms with a diagnosis to a correct treatment. Excising in-office screeners that may be able to engage with somatization patients via a face-to-face interaction may take too much time to be practical.

Even after identifying a somatization patient, it may be difficult to engage the patient in mental health therapies as treatment for their disorder. First, somatization patients may resist treatment in the form of mental health therapy for several reasons. Somatization patient may feel stigmatized by a mental health diagnosis or a suggestion that their symptoms are "in their head". Additionally, somatization patients may be concerned with the cost of mental health treatments and the time commitment of weekly hour-long therapy sessions. Further, somatization patients may be concerned with their privacy. Also, somatization patients may be skeptical about the efficacy of mental health therapies in treating their symptoms. This may be in part due to a lack of education about the effectiveness of mental health therapies in treating symptoms, and the general stigma of mental health interventions.

Since physicians are not mental health specialists, and lack the time necessary to learn and administer mental health treatments for somatization patients. Physicians may be uncomfortable referring somatization patients to a mental health specialist and may become concerns that the patient/doctor relationship may be jeopardized if the patient perceives they are not taking the symptoms seriously. The added time the referral could take combined with a lack of information regarding reliable referral sources that can deliver evidence based intervention for somatization patients, may further reduce a physician's propensity for administering mental health referrals.

Thus, health plans themselves, and not just the physicians, may be unable to effectively engage with this patient group. These patients fly under the radar of payers today. They are not on the case management radar because their individual spending is not high enough. They are not actively managed by disease management because they generally do not have one of the key chronic diseases that would make one a target. And these patients do not tend to engage wellness programs because they do not associate themselves with the well and are often quite concerned with their frailty.

The inventors herein have recognized the issues described above and have devised systems and methods for at least partly addressing the issues. In particular, systems and methods for a somatization identification and treatment platform are provided. In one example, a method comprises receiving medical claims data for a plurality of patients, identifying somatization patients based on the received medical claims data, where the somatization patients include patients suffering from one or more physical symptoms that are in excess of demonstrable disease, presenting a symptom support plan to the identified somatization patients via a user interface based on a severity of their disorder, where the symptom support plan may include one or more of educational programs, episodic support, and behavioral health therapy, monitoring identified somatization patients' progress in the symptom support plan, and displaying the patient's progress to a health plan provider.

In this way, the proficiency in identifying somatization patients may be increased. Additionally, somatization patients may be provided with education tools and information about the benefits of receiving behavioral health therapy for treating their disorder. As a result, they may be more inclined to seek treatment options that will more effectively mitigate their symptoms. By more efficiently identifying somatization patients, and increasing their engagement in proper treatment options, the amount of time and money spend on unproductive treatments for these patients may be reduced. As such, health care costs for both health plan providers, and patients may be reduced.

The above summary is provided to introduce a selection of concepts in a simplified form that are further described below in the Detailed Description. This summary is not intended to identify key features or essential features of the subject matter, nor is it intended to be used to limit the scope of the subject matter. Furthermore, the subject matter is not limited to implementations that solve any or all of the disadvantages noted above or in any part of this disclosure.

DETAILED DESCRIPTION

The present description relates to systems and methods for identification and treatment of somatization patients. A health care system, such as the health care system shown in FIG. 1, may comprise a medical provider, patients, health plan provider, and a somatization system. The somatization system may be configured to identify somatization patients, and recommend treatment for those patients. As described in FIG. 2 the somatization system may comprise one or more computing devices capable of transmitting information between the components of the health care system.

In some examples, somatization patients may self-identify themselves. FIG. 4 shows an example method, for engaging a self-identified somatization patient in a treatment program. However, in other examples, where somatization patients do not self-identify themselves, the somatization system may execute a method, such as the method described in FIG. 3, for identifying somatization patients. In still further examples, the somatization system may identify somatization patients based on data from an accountable care organization by executing a method, such as the method described in FIG. 5.

Figure 7:
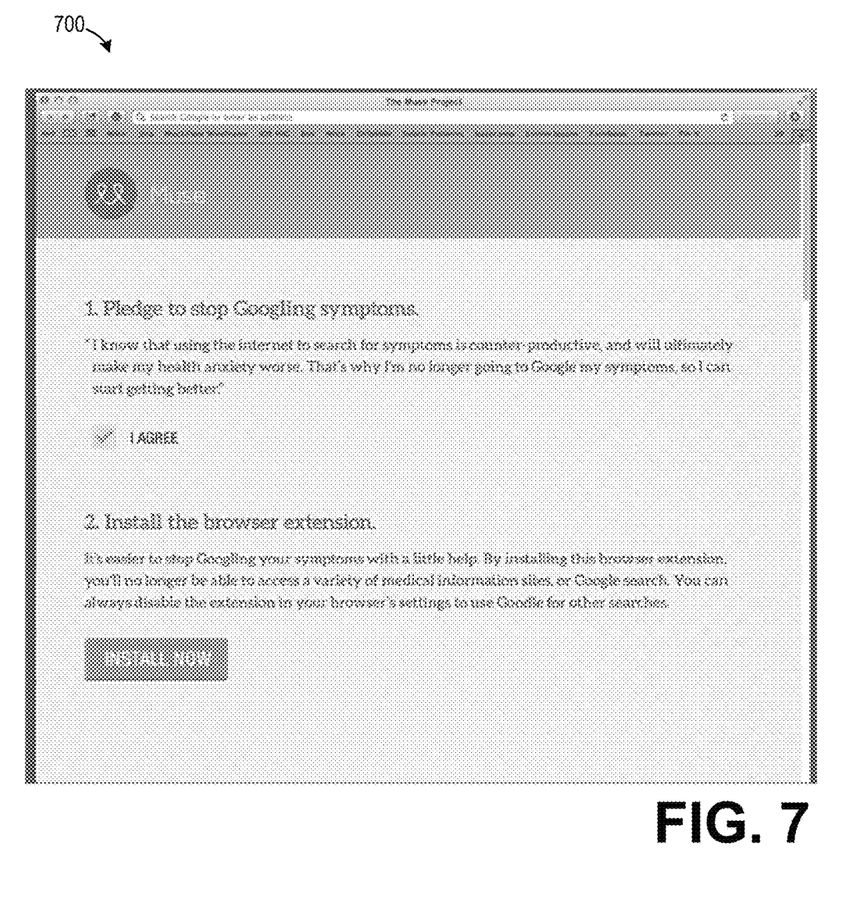
FIG. 7 shows an example interface for a browser plug-in tool, in accordance with an embodiment of the present disclosure.
Figure 8:
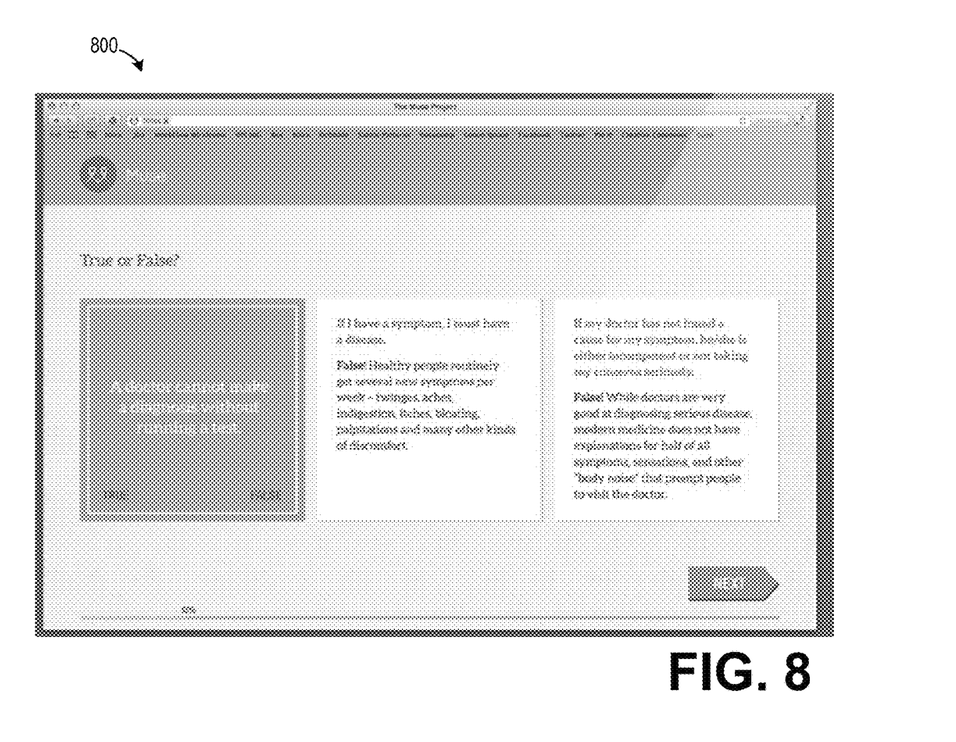
FIG. 8 shows an example interface for a self-paced online learning program, in accordance with an embodiment of the present disclosure.
Figure 9:
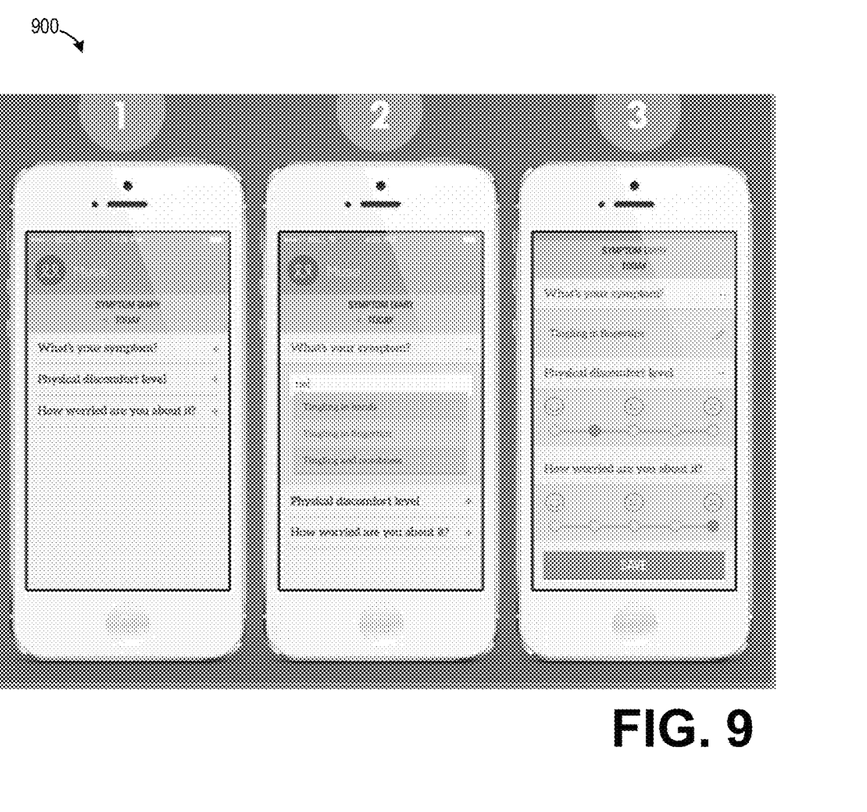
FIG. 9 shows a set of example interfaces for a symptom monitoring application, in accordance with an embodiment of the present disclosure.

After identifying somatization patients, the somatization system, may then recommend and engage the patients in a treatment program. The treatment program may include educational tools, for informing the patients about the effectiveness of behavioral health therapy in alleviating their symptoms. Further, the patient may engage in the treatment program, may learn more about treatment options through interactions with other similar patients, mental health professional, etc. FIGS. 7-9 show example user interfaces that may be presented to a somatization patient during the treatment program. The somatization system may also keep track of a patient's involvement in the treatment program, and may report a patient's progress to a health care plan provider. As such, the effectiveness of the treatment plan may be monitored by the somatization system.

Figure 1:
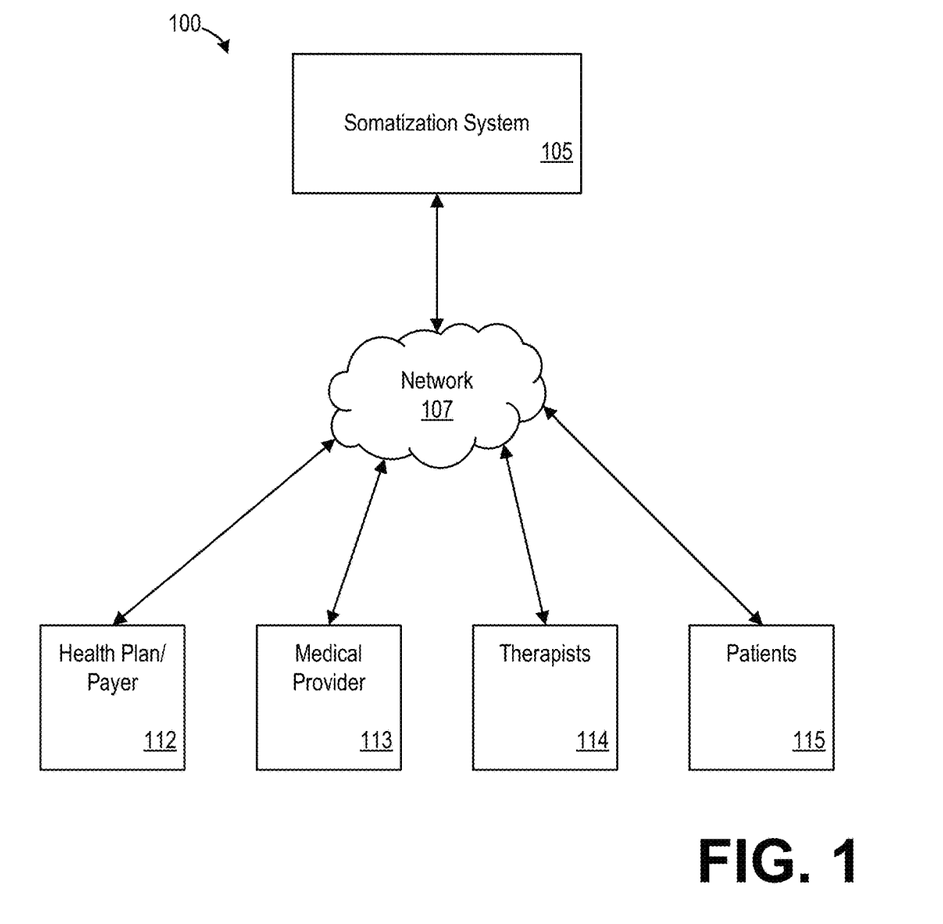
FIG. 1 shows a high-level block diagram of an example online healthcare platform, in accordance with an embodiment of the present disclosure.

FIG. 1 shows a high-level diagram illustrating an example health care system 100 in accordance with the current disclosure. In particular, health care system 100 illustrates a somatization system 105 that may be in communication with one or more of a health plan 112, medical provider 113, therapists 114, and patients 115 through a network 107. The somatization system 105 may identify somatization patients based on claims data received from the medical provider 113. Further, the somatization system 105 may recommend symptom support options to the patients 115 based on the identification of the patients 115 as being somatization patients. In some examples, the somatization system 105 may operate in conjunction with the medical provider 113 and/or therapists or coaches 114 o recommend and provide treatment options to the patients 115. If patients 115 engage in a treatment program, their progress in said program may be monitored and reported to the medical provider 113.

Figure 2:
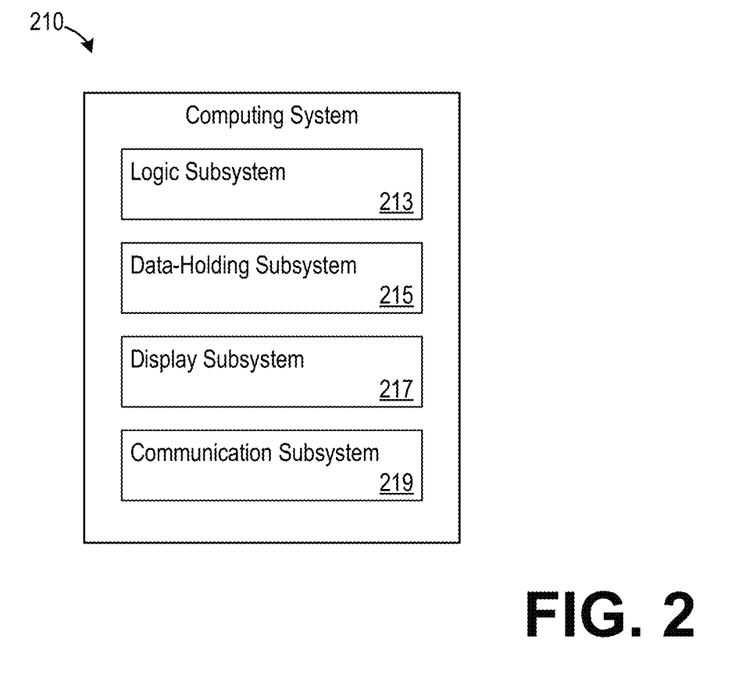
FIG. 2 shows a block diagram of an example computing device, in accordance with an embodiment of the present disclosure.

As described further herein with regard to FIG. 2, each component of health care system 100 depicted in FIG. 1 may represent one or more computing devices capable of transmitting information, and the interactions between components may represent the flow of information between each computing device. As such, health care system 100 may be considered a computing environment in accordance with the current disclosure. Each computing device, such as the somatization system is shown in simplified form. However, each computing device in health care system 100 may take the form of one or more personal computers, server computers, tablet computers, home entertainment computers, network computing devices, mobile computing devices, mobile communication devices, and/or other computing devices. Each computing device in health care system 100 may include one or more displays for displaying an interface.

Health care professionals may provide care to consumers and bill for these services using Current Procedural Terminology (CPT) codes that describe the medical procedures and physicians services provided to the patient.

Payers traditionally only look at case management, disease management, and utilization management (diagnosis, procedure, or dollar-driven) as the source of avoidable spending. The present system uncovers a new category that is non-disease-specific, and accounts for ten cents of every health care dollar. Previous somatization systems do not know how to identify somatization patients. Physicians struggle to identify these patients, as these patients visit numerous providers. Patients do not auto-identify themselves, as they do not link physical symptoms with health anxiety. Employers have less productive employees due to absenteeism or illness. Traditional in-office screeners take too much time and are not an established screening tool in practices.

A somatization system algorithm, which may include computer readable instructions stored in non-transitory memory of the somatization system, may be configured for identifying and flagging somatization patients for referral and treatment. In some examples, the algorithm may include an in-office screener that identifies and flags patients for referral and treatment. A self-screener helps patients identify their problems and self-refer.

Somatization patients resist mental health referrals. Physicians are uncomfortable with referring to mental health for such patients, as well as with how much additional time a difficult referral could take. Physicians lack reliable referral resources who can deliver evidence-based intervention for such patients. Physicians are under pressure to continue providing medical services well past the point of medical necessity due to lack of alternatives. Patients feel stigmatized by mental health diagnosis. Patients are concerned with cost. Patients are concerned about privacy. The traditional way to deliver referral has poor follow through due to: insurance benefits, not easy to schedule, etc.

The Somatization system is positioned as symptom support rather than therapy for maximum patient engagement and to reduce the stigma. The Somatization system also provides training tools to providers to teach them how to make referrals quickly and comfortably. In-office scheduling through the Somatization system allows for increased patient follow through. Patients receive treatment from the comfort of their own home using HIPAA-secure video messaging.

Physicians do not have the skill to treat somatization patients, as these patients do not have a structural physical disease. Physicians who are not mental health specialists also lack time to learn and administer these treatments. Integrated behavioral health is not set for lengthy interventions. Community mental health counselors are generally trained in generic cognitive behavior therapy and do not have access to the specialized form of treatment that is required. Providers feel discouraged from referring patients to community therapists because non-specialized treatments backfire. Furthermore, providers are dissatisfied with community mental health referrals because the providers do not receive feedback on patient progress. Patients also lack faith that treatment is viable.

The Somatization system provides specialized evidence-based treatment. A network of specially-trained therapists and coaches deliver a treatment protocol. The Somatization system comprises a virtual behavioral health treatment system which is tightly integrated with existing healthcare systems and provides feedback on patient progress. The Somatization system also provides patient testimonials for patients with similar conditions in order to instill hope.

Payers need proof that the Somatization system lowers utilization and healthcare costs. Patients need proof that they can be successfully treated. Providers need proof that referring patients to the program will benefit their practice and make patients healthier.

The Somatization system includes tracking, reporting, and analytics to provide proof points and validate results.

FIG. 2 schematically shows a non-limiting computing system 210 that may perform one or more of the methods and processes described herein. As described hereinabove, any of the components shown in FIG. 1 may comprise computing system 210. It is to be understood that virtually any computer architecture may be used for a computing device without departing from the scope of this disclosure. In different embodiments, computing system 210 may take the form of a mainframe computer, server computer, desktop computer, laptop computer, tablet computer, home entertainment computer, network computing device, mobile computing device, mobile communication device, gaming device, etc.

Computing system 210 includes a logic subsystem 213 and a data-holding subsystem 215. Computing system 210 may optionally include a display subsystem 217, communication subsystem 219, and/or other components not shown in FIG. 2. For example, computing system 210 may also optionally include user input devices such as keyboards, mice, game controllers, cameras, microphones, and/or touch screens.

Logic subsystem 213 may include one or more physical devices configured to execute one or more instructions. For example, logic subsystem 213 may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

Logic subsystem 213 may include one or more processors that are configured to execute software instructions. Additionally or alternatively, the logic subsystem 213 may include one or more hardware or firmware logic machines configured to execute hardware or firmware instructions. Processors of the logic subsystem 213 may be single core or multi-core, and the programs executed thereon may be configured for parallel or distributed processing. The logic subsystem 213 may optionally include individual components that are distributed throughout two or more devices, which may be remotely located and/or configured for coordinated processing. One or more aspects of the logic subsystem 213 may be virtualized and executed by remotely accessible networked computing devices configured in a cloud computing configuration.

Data-holding subsystem 215 may include one or more physical, non-transitory devices configured to hold data and/or instructions executable by the logic subsystem 213 to implement the herein described methods and processes. When such methods and processes are implemented, the state of data-holding subsystem may be transformed (for example, to hold different data).

Data-holding subsystem 215 may include removable media and/or built-in devices. Data-holding subsystem 215 may include optical memory (for example, CD, DVD, HD-DVD, Blu-Ray Disc, etc.), and/or magnetic memory devices (for example, hard disk drive, floppy disk drive, tape drive, MRAM, etc.), and the like. Data-holding subsystem 215 may include devices with one or more of the following characteristics: volatile, nonvolatile, dynamic, static, read/write, read-only, random access, sequential access, location addressable, file addressable, and content addressable. In some embodiments, logic subsystem 213 and data-holding subsystem 215 may be integrated into one or more common devices, such as an application specific integrated circuit or a system on a chip.

It is to be appreciated that data-holding subsystem 215 includes one or more physical, non-transitory devices. In contrast, in some embodiments aspects of the instructions described herein may be propagated in a transitory fashion by a pure signal (for example, an electromagnetic signal, an optical signal, etc.) that is not held by a physical device for at least a finite duration. Furthermore, data and/or other forms of information pertaining to the present disclosure may be propagated by a pure signal.

When included, display subsystem 217 may be used to present a visual representation of data held by data-holding subsystem 215. As the herein described methods and processes change the data held by the data-holding subsystem 215, and thus transform the state of the data-holding subsystem 215, the state of display subsystem 217 may likewise be transformed to visually represent changes in the underlying data. Display subsystem 217 may include one or more display devices utilizing virtually any type of technology. Such display devices may be combined with logic subsystem 213 and/or data-holding subsystem 215 in a shared enclosure, or such display devices may be peripheral display devices.

When included, communication subsystem 219 may be configured to communicatively couple computing system 210 with one or more other computing devices. Communication subsystem 219 may include wired and/or wireless communication devices compatible with one or more different communication protocols. As non-limiting examples, communication subsystem 219 may be configured for communication via a wireless telephone network, a wireless local area network, a wired local area network, a wireless wide area network, a wired wide area network, etc. In some embodiments, communication subsystem 219 may allow computing system 210 to send and/or receive messages to and/or from other devices via a network such as the public Internet.

Figure 3:
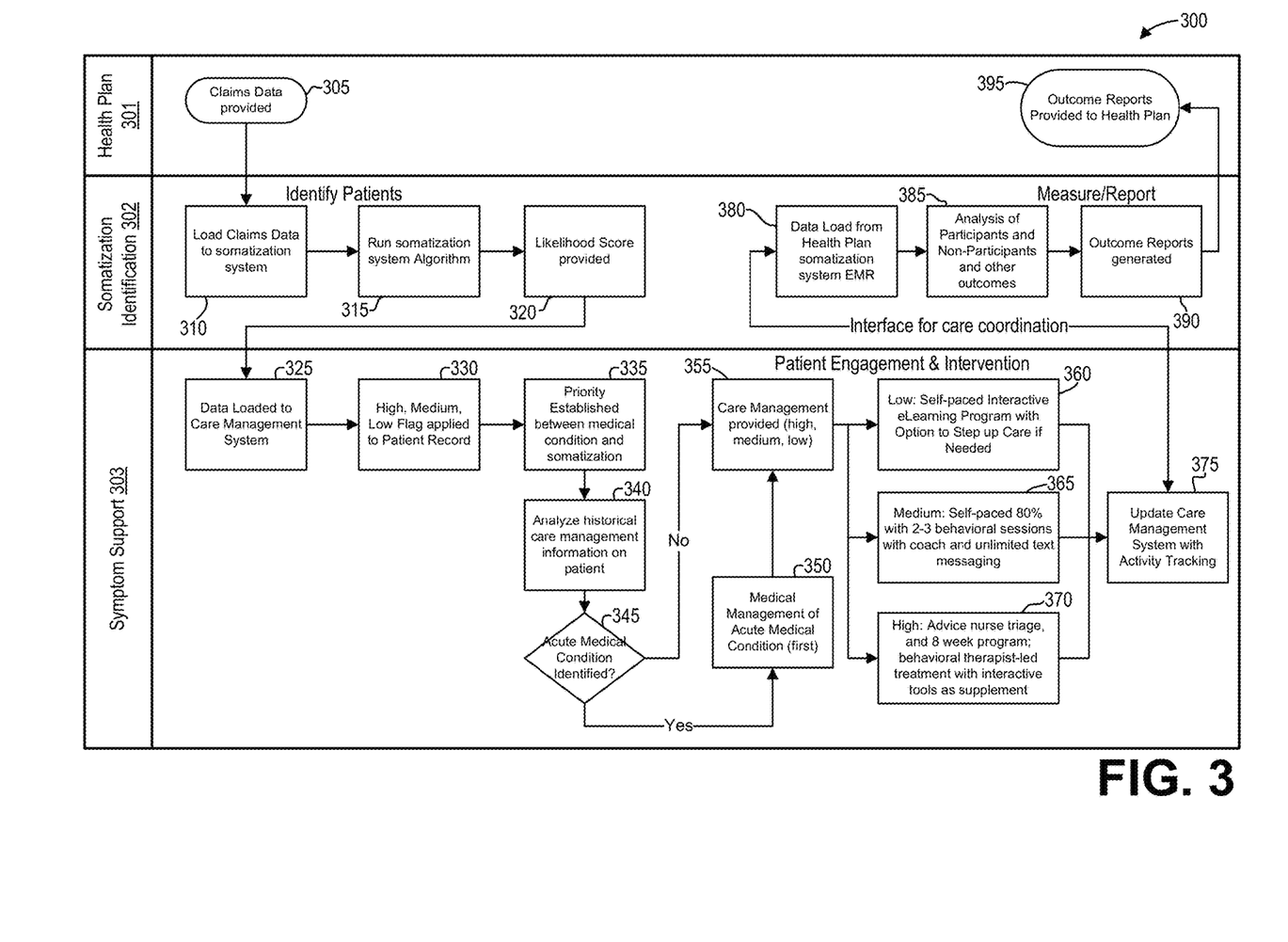
FIG. 3 shows a flow chart of an example method for identifying a somatization patient, in accordance with an embodiment of the present disclosure.
Figure 4:
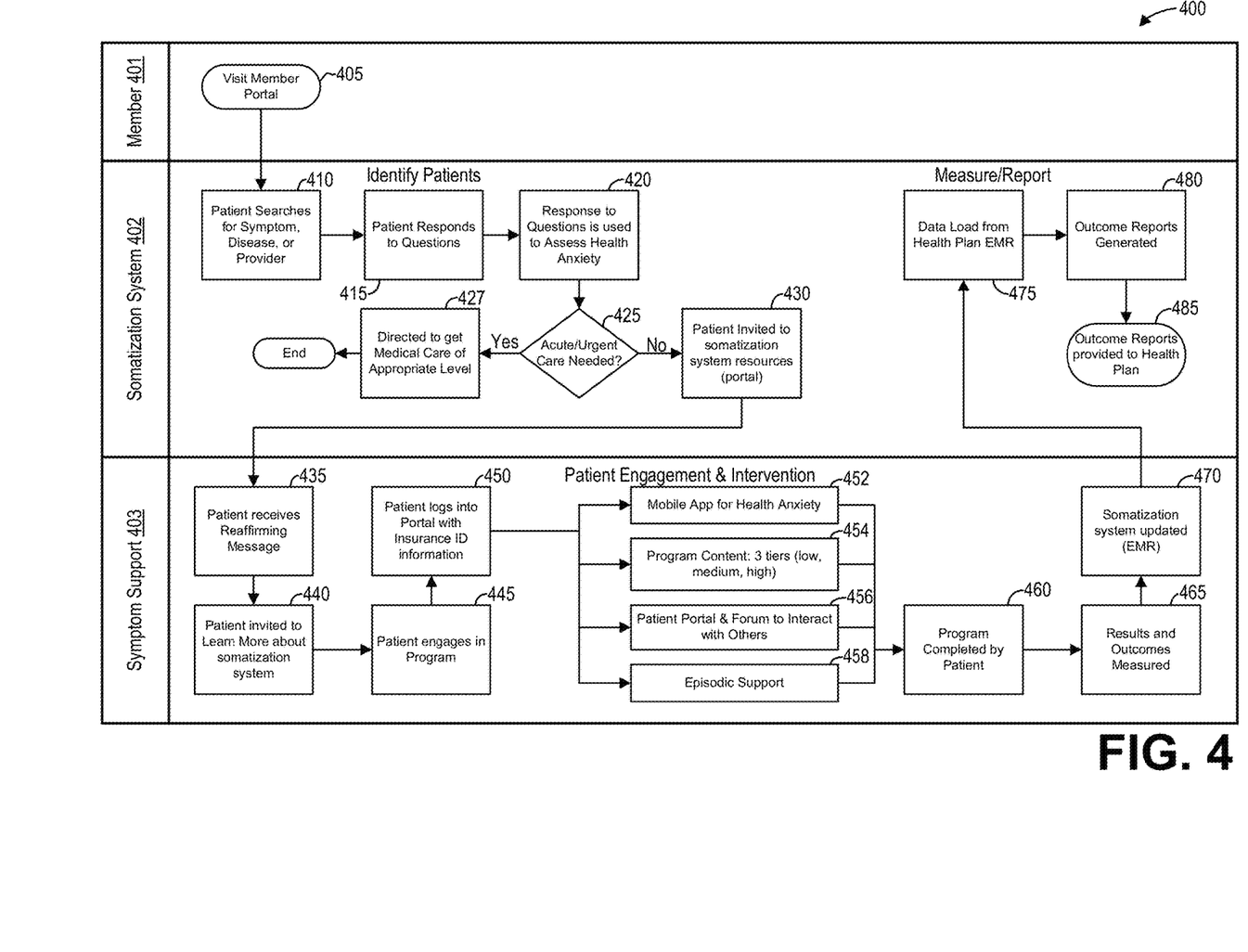
FIG. 4 shows a flow chart of an example method for engaging a self-identified somatization patient in a treatment program, in accordance with an embodiment of the present disclosure.

FIG. 3 shows a high-level flow chart illustrating an example method 300 for identifying health plan members experiencing somatization according to an embodiment.

Method 300 begins at 305. At 305, claims data is provided by the health plan 301 to the somatization identification system 302. The somatization identification system 302 may be somatization system 105 shown above with reference to FIG. 1. At 310, the somatization identification system loads the claims data for processing. At 315, somatization identification system processes the claims data using a somatization system algorithm. At 320, the somatization identification system generates a likelihood score based on the output of the somatization system algorithm, and provides this likelihood score to the symptom support system 303 of the somatization system (e.g., somatization system 105 shown in FIG. 1). Thus, the somatization system may comprise both the symptom support system 303 and the somatization identification system 302. Thus, in some examples, both the symptom support system 303 and somatization identification system 302 may be included in the somatization system 105. However, in other examples, the symptom support system 303 may be the somatization system 105 shown above with reference to FIG. 1.

At 325, the symptom support system 303 loads the likelihood score data. At 330, the symptom support system 303 applies a high, medium, or low flag to a medical record for the patient. The high, medium, and low flags indicate the likelihood score for the patient, and alerts a medical provider viewing the patient's medical record of the patient's likelihood score.

At 335, priority is established between the medical condition and somatization.

At 340, the symptom support system 303 analyzes historical care management information for the patient.

At 345, the symptom support system 303 determines if an acute medical condition is identified. If yes, then medical management of the acute medical condition is provided at 350. After providing the medical management, or if no acute medical condition is identified, method 300 proceeds to 355. At 355, care management is provided based on the high, medium, or low flag applied to the patient's medical record.

If the medical record includes a low flag, at 360 the low treatment is provided to the patient. In particular, the low treatment includes a self-paced interactive eLearning program with an option to step up care if needed.

If the medical record includes a medium flag, at 365 the medium treatment is provided to the patient. In particular, the medium treatment includes a self-paced interactive eLearning program for 80% of the treatment, with a several (e.g., 2-3) behavioral sessions provided to the patient during a predetermined time period (e.g., weekly, monthly, bimonthly, etc.). The behavioral sessions are provided in-person by a coach. In some examples, the system enables the patient with unlimited text messaging with the coach.

If the medical record includes a high flag, at 370 the high treatment is provided to the patient. In particular, the high treatment includes, per advice from a nurse triage, a treatment program which lasts for a predetermined time period (e.g., 4-12 weeks). The treatment program is carried out by a behavioral therapist. The treatment program is supplemented by interactive tools via the Somatization system.

After (or in some examples, while) the appropriate treatment program is provided to the patient, method 300 proceeds to 375. At 375, treatment activity is tracked and updated into the care management system.

At 380, the activity data tracked by the somatization system is loaded into the somatization identification system. Specifically, the data is loaded from the health plan electronic medical record (EMR). At 385, the somatization identification system 302 analyzes the activity data from participants, non-participants, and other outcomes (e.g., from previous analyses). At 390, the somatization identification system 302 generates outcome reports based on the analysis performed at 385.

At 395, the somatization identification system 302 provides the outcome reports to the health plan. Method 300 ends thereafter.

FIG. 4 shows a high-level flow chart illustrating an example method 400 for health plan members who self-identify their somatization.

Method 400 begins at 405. At 405, a member 401 (referred to hereinafter as a patient) visits the member portal for the somatization system 402. At 410, within the member portal, the patient searches for symptoms, diseases, or providers. At 415, the patient responds to questions provided by the somatization system 402. At 420, the somatization system 402 assess health anxiety of the patient based on the patient's response to the questions.

At 425, the somatization system 402 determines if acute and/or urgent care is needed. If yes, method 400 proceeds to 427. At 427, the patient is directed to obtain medical care at the appropriate level needed. Method 400 then ends.

Returning to 425, if acute and/or urgent care is not needed, method 400 proceeds to 430. At 430, the patient is invited to a resources portal through which the patient may access the symptom support program 403.

At 435, the patient receives a reaffirming message. The reaffirming message may be specifically tailored to the patient based on the level of health anxiety assessed at 420. At 440, the patient is invited to learn more about symptom support program 403. At 445, the patient engages in the symptom support program 403. Engaging in the symptom support program 403 may comprise establishing a user account in the Somatization system 402. In some examples, the somatization system 402 may include the symptom support program 403.

At 450, the patient logs into the somatization system portal with insurance identification information. Within the somatization system portal, multiple resources are provided to the patient.

As a non-limiting example, at 452 the symptom support program 403 provides a mobile application (e.g., an executable program configured for a mobile device such as a smartphone or tablet) for managing health anxiety.

As another non-limiting example, at 454 the symptom support program 403 provides tiered program content. In particular, the symptom support program may provide, as an illustrative example, three levels of program content. Example levels of program content are described herein above with regard to FIG. 3 at 360, 375, and 375.

As another non-limiting example, at 456 the symptom support program 403 provides a patient portal and forum wherein the patient may interact with other patients, therapists, providers, and so on.

As another non-limiting example, at 458 the symptom support program provides episodic support for the patient.

At 460, the symptom support program is completed by the patient. At 465, results and outcomes of the program are measured. At 470, the symptom support program 403 updates the EMR for the patient with the results and outcomes.

At 475, the somatization system 402 loads data from the updated EMR. At 480, outcome reports are generated. At 485, outcome reports are provided to the health plan for review. Method 400 then ends.

Figure 5:
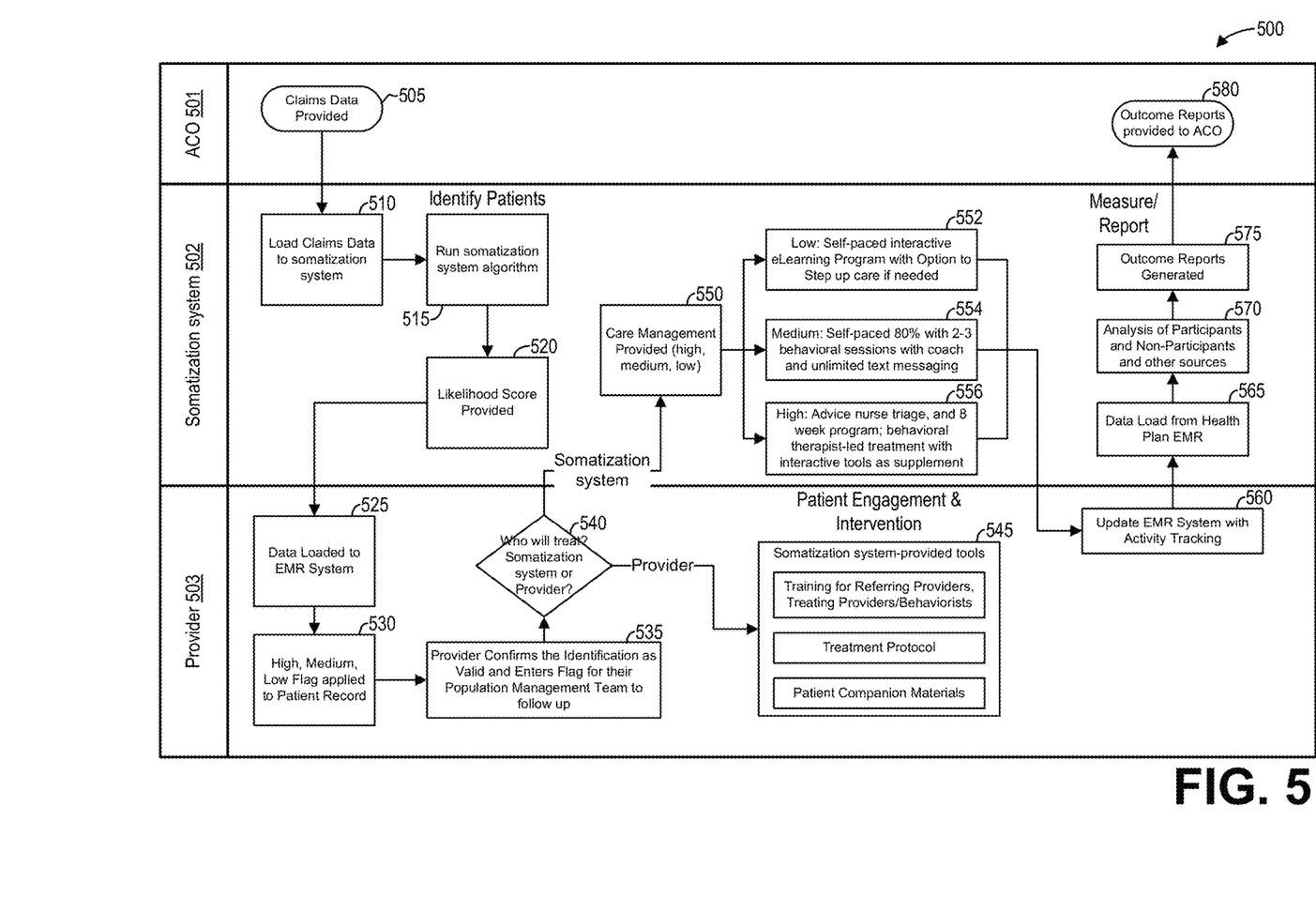
FIG. 5 shows a flow chart of an example method for identifying patients experiencing somatization in accordance with an embodiment of the present disclosure.

FIG. 5 shows a high-level flow chart illustrating an example method 500 for accountable care organizations (ACOS) identifying patients experiencing somatization according to an embodiment.

Method 500 begins at 505. At 505, the ACO 501 provides claims data to the somatization identification system 502. At 510, the somatization system 502 loads claims data. At 515, the somatization system 502 runs the somatization system algorithm using the loaded claims data as input. At 520, the somatization system 502 provides the likelihood score generated by the somatization system algorithm at 515 to the provider 503.

At 525, the provider 503 loads the likelihood score into the EMR system. At 530, a high, medium, or low flag is applied to the patient's electronic medical record (EMR). At 535, the provider 503 confirms the identification as valid and enters the flag for their population management team to follow up.

At 540, the provider 503 determines if the provider 503 or the somatization system 502 will provide treatment to the patient. If the provider chooses to provide treatment, method 500 proceeds to 545. At 545, the provider may utilize multiple somatization system-provided tools to treat the patient. Such tools include training for referring providers, treating providers, behaviorists, and so on. The tools also include an evidence-based treatment protocol. The tools also include companion materials for the patient. One or more of the tools may be provided to the provider 503 by the somatization system 502.

Returning to 540, if the provider decides that the somatization system will provide treatment, method 500 proceeds to 550. At 550, the somatization system 502 provides care management based on the high, medium, or low flag applied to the EMR. As a non-limiting example, at 552 the somatization system 502 provides low treatment. The low treatment includes a self-paced interactive eLearning program with an option to step up care if needed. Stepping up care comprises providing a medium or high treatment, as described further herein.

As another non-limiting example, at 554 the somatization system 502 provides medium treatment. Medium treatment includes self-paced interactive eLearning program for 80% of the treatment, and with several in-person behavioral sessions (e.g., 2-3) with a coach and unlimited text messaging between the patient and the coach.

As yet another non-limiting example, at 556 the somatization system 502 provides, per an advice nurse triage, a treatment program which lasts for a predetermined amount of time (e.g., 6-10 weeks). The treatment program includes behavioral therapist-led treatment with interactive tools provided at 552 and 554 as a supplement.

After the appropriate level of treatment is provided, the EMR system is updated with activity data tracked by the somatization system 502. At 565, the somatization system 502 loads activity data from the EMR system. At 570, the somatization system 502 analyzes the activity of participants, non-participants, and other sources (e.g., previous outcomes). At 575, the somatization system 502 generates outcome reports. At 580, the somatization system 502 provides the outcome reports to the ACO 501. Method 500 then ends.

Figure 6:
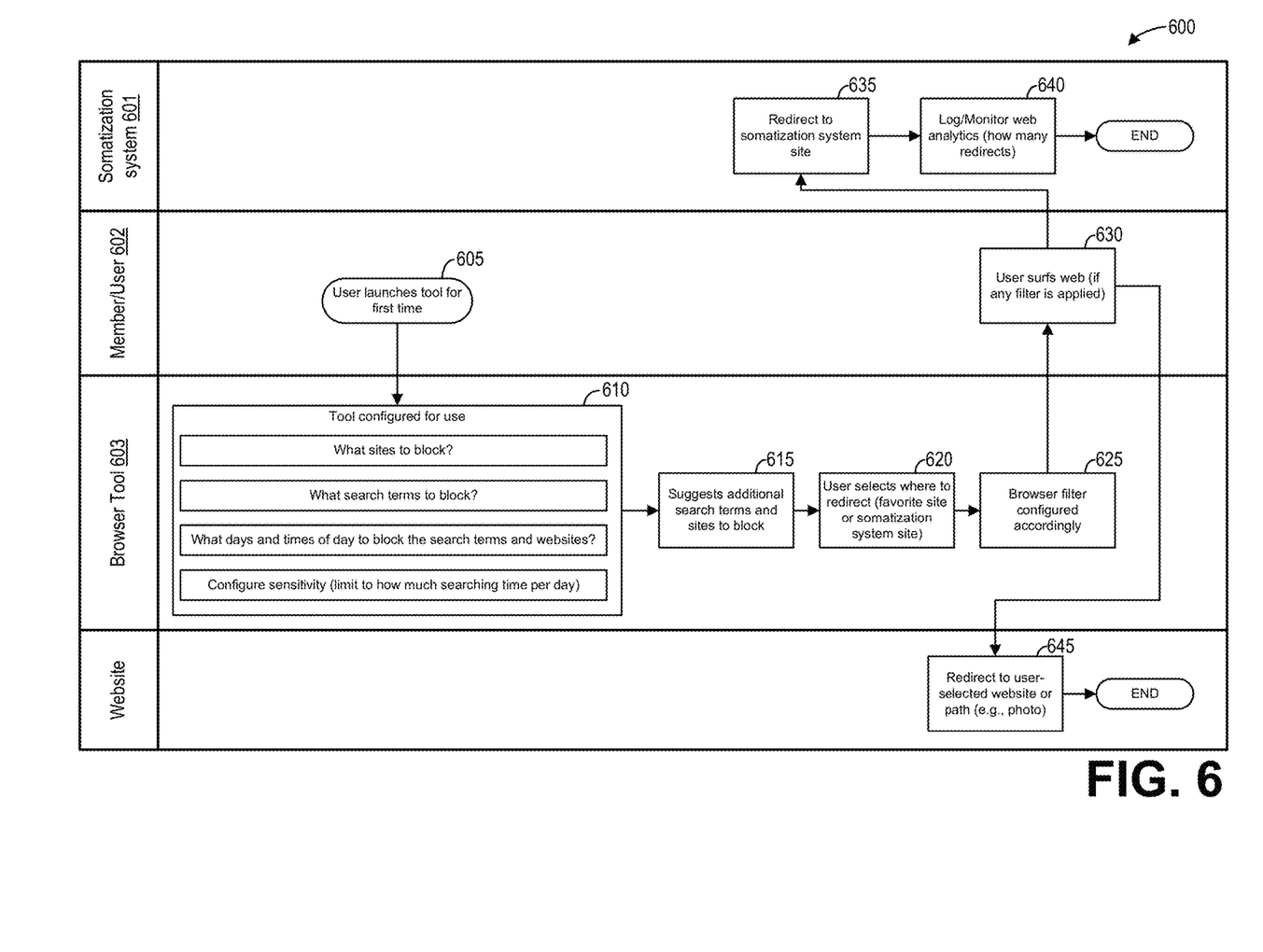
FIG. 6 shows a high-level flow chart illustrating an example method for a browser plug-in tool, in accordance with an embodiment of the present disclosure.

FIG. 6 shows a high-level flow chart illustrating an example method 600 for a browser plug-in tool according to an embodiment.

Method 600 begins at 605. At 605, the user 602 launches the browser plug-in tool 603 for the first time. At 610, the browser plug-in tool 603 is configured for use. Configuring the browser plug-in tool 603 includes several steps. As non-limiting example, configuring the browser plug-in tool 603 includes determining which sites to block, which search terms to block, what days and times of day to block the indicated sites and search terms, and so on. Configuring the browser plug-in tool further includes configuring the sensitivity of the browser plug-in tool. For example, the browser plug-in tool may be limited to how much searching time per day the plug-in tool blocks the indicated sites and search terms. Alternatively, the browser plug-in tool may allow a certain amount of searching prior to blocking the indicated sites and search terms.

At 615, the browser plug-in tool 603 suggests additional search terms and sites to block based on the indicated sites and search terms. At 620, the user 602 selects where the browser plug-in tool should redirect (e.g., a favorite site of the user or a website for the Somatization system). At 625, the browser filter is configured according to the preceding actions.

At 630, the user 602 surfs the web. If any filter is applied, the browser plug-in tool 603 will redirect the user 602 based on the configuration of the browser plug-in tool 603. For example, if the user selected a default setting (e.g., the somatization system site), the user 602 is redirected to the somatization system site at 635. The somatization system 601 monitors and/or logs web analytics (e.g., how many redirects for a particular user 602). Method 600 then ends.

As another example, if the user selected a favorite site at 620, the browser plug-in tool redirects the user 602 to the website 604 at 645. Method 600 then ends.

FIG. 7 shows an example interface 700 for a browser plug-in tool according to an embodiment. In particular, interface 700 includes a prompt for a user to pledge to stop searching for symptoms online. In addition, interface 700 includes a link to install the browser plug-in tool, which assists the user in following through with the pledge.

FIG. 8 shows an example interface 800 for a self-paced interactive eLearning program according to an embodiment. Interface 800 includes a variety of questions relating to behavioral and physical health. In some examples, one or more of the variety of questions may be binary (e.g., true or false) questions. As depicted, the user may select an answer (e.g., true or false) to a question prompt. After the user selects an answer, the interface displays the correct answer in addition to an explanation of the correct answer. The interface 800 may further include a progress bar which enables a user to track his or her progress through the program.

FIG. 9 shows a set of example interfaces 900 for a symptom monitoring application according to an embodiment, where the set of example interfaces 900 includes an interface 1, interface 2, and interface 3. In particular, the symptom monitoring application comprises a symptom diary which enables a user/patient to track his or her symptoms on a daily basis.

For example, interface 1 displays a set of example questions regarding a user's symptoms. After the user selects one of the questions, the user may input a response. Interface 2 shows an example response input. As depicted, the interface may display auto-completed responses, which may assist the user in specifically defining his or her symptoms. Responses to other questions may or may not include text input as depicted in interface 2. For example, interface 3 shows a sliding bar for user input. The user may select a point on the sliding bar corresponding to his or her physical discomfort level and anxiety level, as non-limiting examples. After inputting these responses, the Somatization system may collect the responses for analysis. In this way, the user's symptoms, physical discomfort levels, and anxiety levels may be monitored over time, which allows the documentation and analysis of a user's progress during treatment.

A technical effect of reducing health care costs is achieved by more quickly and efficiently identifying somatization patients. By monitoring and assessing a patient's medical activity, such as their health care costs, medical bills, hospital visits, etc., a predictive model may be generated to determine if the patient suffers from a medically undiagnosed conditions. Thus, by aggregating and analyzing patient medical activity data, the rate at which somatization patients are identified may be increased. By more quickly identifying somatization patients, health care costs for those individuals may be reduced. Further, another technical effect of increasing patient safety and health may be achieved by more quickly identifying somatization patients and by prescribing proper treatment plans for said patients.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
receiving medical insurance claims data for a plurality of patients at a somatization system server;
at the somatization system server, executing instructions stored in non-transitory memory to run a somatization system algorithm on the medical insurance claims data to compare the received medical insurance claims data to identify somatization patients with physical symptoms that are in excess of demonstrable disease based on a likelihood score generated by the somatization system algorithm, the likelihood score related to a severity of an identified somatization patients' disorder as determined via the comparing the received medical insurance claims data;
via the instructions stored at the somatization system server, providing a specialized symptom support treatment to the identified somatization patients where the specialized symptom support treatment includes one or more of educational programs, episodic support, mental health therapy, and an internet browser plug-in tool with instructions based on the specialized symptom support treatment that include blocking one or more of internet sites and/or internet search terms; and
tracking activity data related to progress of the identified somatization patients receiving the specialized symptom support treatment.

2. The method of claim 1, wherein the educational programs include information about somatic system disorder and research concerning effectiveness of mental health therapy in alleviating symptoms associated with the disorder.

3. A method, comprising:
at a somatization system server, receiving medical insurance claims data for a patient and executing instructions stored in non-transitory memory to run a somatization system algorithm on the medical insurance claims data to generate an output that estimates a somatization likelihood that the patient is suffering from one or more physical symptoms that are in excess of demonstrable disease; and
via the somatization system server, providing a specialized symptom support treatment comprising a high, a medium, or a low specialized symptom support treatment to the patient via a user interface as a function of the somatization likelihood, wherein providing the specialized symptom support treatment includes monitoring patient progress to the specialized symptom support treatment and providing the patient's progress to a health plan provider, wherein providing the specialized symptom support treatment includes providing an internet browser plug-in tool, the internet browser plug-in tool configured to block one or more of internet sites and internet search terms.

4. The method of claim 3, wherein monitoring patient progress includes generating an alert when the patient deviates from the specialized symptom support treatment, and wherein the alert is provided to the health plan provider.

5. The method of claim 3, wherein monitoring patient progress includes generating a report based on the patient's adherence to the specialized symptom support treatment, and wherein the report is provided to the health plan provider.

6. The method of claim 3, wherein the specialized symptom support treatment comprises a treatment the patient has not previously received.

7. The method of claim 3, wherein the specialized symptom support treatment does not include a medication.

8. The method of claim 3, wherein the specialized symptom support treatment comprises mental health treatment.

9. A system, comprising:
a somatization system server including computer readable instructions stored in non-transitory memory for:
retrieving medical insurance claims data;
running a somatization system algorithm on the medical insurance claims data to identify a somatization patient suffering from one or more physical symptoms that are in excess of demonstrable disease based on a somatization likelihood that is output by the somatization system algorithm;
providing a specialized symptom support treatment for the somatization patient based on the somatization likelihood, the specialized symptom support treatment including one or more of educational programs, episodic support, mental health therapy, and an internet browser plug-in tool with instructions based on the specialized symptom support treatment that include blocking one or more of internet sites and/or internet search terms,
wherein providing the specialized symptom support treatment for the patient includes monitoring a progress of the somatization patient to the specialized symptom support treatment and displaying the progress to a health plan provider.

10. The method of claim 1, wherein identifying the somatization patients via comparing the received medical insurance claims data increases a rate at which the somatization patients are identified and reduces health care costs.

11. The method of claim 3, wherein the patient receives the specialized symptom support treatment via health insurance portability and accountability act (HIPAA)-secure video messaging.

12. The method of claim 3, wherein the patient suffering from the one or more physical symptoms in excess of demonstrable disease is due to a mental disorder of the patient.

13. The method of claim 3, wherein the low specialized symptom support treatment comprises a self-paced interactive eLearning program with an option to step up care.

14. The method of claim 3, wherein the medium specialized symptom support treatment comprises at least two or more behavioral sessions provided to the patient during a predetermined time period, the at least two or more behavioral sessions provided in-person by a coach.

15. The method of claim 3, wherein the high specialized symptom support treatment comprises, per advice from a nurse triage, a treatment program lasting a predetermined time period, the treatment program carried out by a behavioral therapist and supplemented by interactive tools.

16. The system of claim 9, wherein the specialized symptom support treatment for the patient is provided via a network of specially-trained therapists and coaches.

* * * * *